United States Patent [19]

Mukherjee et al.

[11] Patent Number: 5,266,562
[45] Date of Patent: Nov. 30, 1993

[54] ANTI-INFLAMMATORY AGENTS

[75] Inventors: Anil B. Mukherjee, Brookville; Lucio A. Miele, Rockville, both of Md.

[73] Assignee: The United States of America as represented by the Secretary of the Department of Health and Human Services, Washington, D.C.

[21] Appl. No.: 122,379

[22] Filed: Nov. 19, 1987

[51] Int. Cl.$^5$ .................. A61K 37/02; C07K 7/08; C07K 7/06
[52] U.S. Cl. ............................. 514/15; 514/14; 514/16; 514/886; 530/326; 530/327; 530/328
[58] Field of Search .............. 530/328, 327, 326; 514/16, 15, 14, 886

[56] References Cited

U.S. PATENT DOCUMENTS 4,810,777 3/1989 Zasloff ................... 530/324

OTHER PUBLICATIONS

The Emko Journal, vol. 2, No. 5, pp. 711–714, 1983.
Biochem. 149, 531–535 (1985), Andreu et al.
The Journal of Biochemical Chemistry, vol. 261, No. 12, pp. 5341–5349, 1986.
Biochem. J. (1987) 243, 113–120, Giovannini et al.
Ialenti et al., Agents Actions, vol. 29(1-2), pp. 48–49, (1990), Chem. Abs. vol. 112(11), 92441b.
Binsburger et al., FEBS Letters, vol. 247, No. 2, pp. 293–297, (1989).
Burger's Medicinal Chemistry, Fourth Edition, Part III, pp. 1214–1219 (1981).
P. H. Cartwright et al., Brit. J. Dermatol. 122 (1990), pp. 277–278.
Chi-Chao Chan et al., Ocular Immunology Today (1990), pp. 467–470.
Chi-Chao Chan et al., Arch. Ophthalmol, vol. 109, Feb. 1991, pp. 278–281.
Mukherjee, et al. *American Journal of Reproductive Immunology* 2:135–141 (1982).
Levin, et al. *Life Sciences* 38:1813–1819 (1986).
Manjunath, et al., *Biochemical Pharmacology* 5:741–746 (1987).
Manjunath, et al., *Biochemical and Biophysical Research Communications* 121: 400–407 (1984).
Mukherjee, et al., *Science* 219:989–991 (1983).
Flower et al., *Nature* 278:456–459 (1979).
Russo-Marie, et al. *Biochem. Biophys. Acta.* 712:277–285 (1982).
Hirata *Advances in Prostaglandin, Thromboxane and Leukotriene Research* 2:73–78 (1983).
Hirata, et al., *Biochem, Biophy Res.* 109:223–230 (1982).
DiRosa et al., *Prostaglandins* 28:441–443 (1984).
Nieto, et al., *Arch. Biochem. Biophys.* 180:82–92 (1977).
Mayol et al., *Endocrinology* 95:1534–1538 (1974).
Stewart et al., *Solid Phase Peptide Synthesis* Pierce Chemical Co. Rockford Ill. (1984).

Primary Examiner—Merrell C. Cashion, Jr.
Assistant Examiner—T. D. Wessendorf
Attorney, Agent, or Firm—Birch, Stewart, Kolasch & Birch

[57] ABSTRACT

Synthetic oligopeptides having potent anti-inflammatory and phospholipase A$_2$ inhibiting properties are described. A method of controlling inflammation of body tissue is also described.

9 Claims, 4 Drawing Sheets

ANTI-INFLAMMATORY AGENTS

BACKGROUND OF THE INVENTION

1. Technical Field

The present invention is related to anti-inflammatory compounds. More particularly, the present invention is related to a new family of synthetic peptides having potent anti-inflammatory activity and a method for controlling or alleviating inflammation.

2. State Of The Art

Inflammatory reactions are involved in a large number of human diseases. Some steroid hormones are well known modulators of inflammation. It has been suggested that the steroids exert their effect by decreasing the level of tissue prostanoids which are known mediators of inflammatory reactions (for review, see Ferreira, *Handbook of Inflammatory Diseases* 5:107–116, 1985). One of the key enzymes controlling the level of arachidonic acid, the substrate for prostaglandin synthesis, is phospholipase $A_2$. A possible mechanism for preventing inflammation is the inhibition of this enzyme, thereby lowering the level of tissue prostanoids (Flower et al, *Nature* 278:456–459, 1979; Russo-Marie et al, *Biochem. Biophys. Acta.* 712:177–185, 1982; and Hirata *Advances in Prostaglandin, Thromoxane and Leukotriene Research* 2:73–78, 1983).

During the past decade several corticosteroid dependent low molecular weight proteins with phospholipase $A_2$ ($PLA_2$) inhibitory activity have been described (Hirata et al, *Biochem. Biophys. Res.* 109:223–230, 1982). Lipocortins (DiRosa et al, *Prostaglandins* 28:441–443, 1984), a family of such inhibitors induced by corticosteroids, are suggested to be the mediators of anti-inflammatory action of these steroids. A genetically different protein, blastokinin, also known as uteroglobin, is a potent $PLA_2$ inhibitor (Levin et al, *Life Sci.* 38:1813–1819, 1986). Heretofore, however, small peptides that consist of 15 or fewer amino acid residues, which include VLDS as a preferred, but not necessarily essential, portion thereof, and that possess potent $PLA_2$ inhibitory and anti-inflammatory activity, such as the antiflammin peptides of this invention, have not been known or described.

SUMMARY OF THE INVENTION

It is, therefore, an object of the present invention to provide a family of peptides having potent anti-inflammatory and $PLA_2$ inhibitory activity. These peptides are designated herein as "antiflammin".

It is another object of the present invention to provide a pharmaceutical composition comprising, as an active ingredient, an anti-inflammatory effective amount of antiflammin; and a pharmaceutically acceptable, non-toxic, sterile, carrier.

It is a further object of the present invention to provide a method for reducing inflammation in a subject or tissue afflicted with inflammatory condition, comprising administering to said subject or contacting the inflamed tissue with anti-inflammatory amount of antiflammin in one or more dosage as tolerated by said subject.

Other objects and advantages of the present invention will become apparent from the following Detailed Description of the Invention.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1:
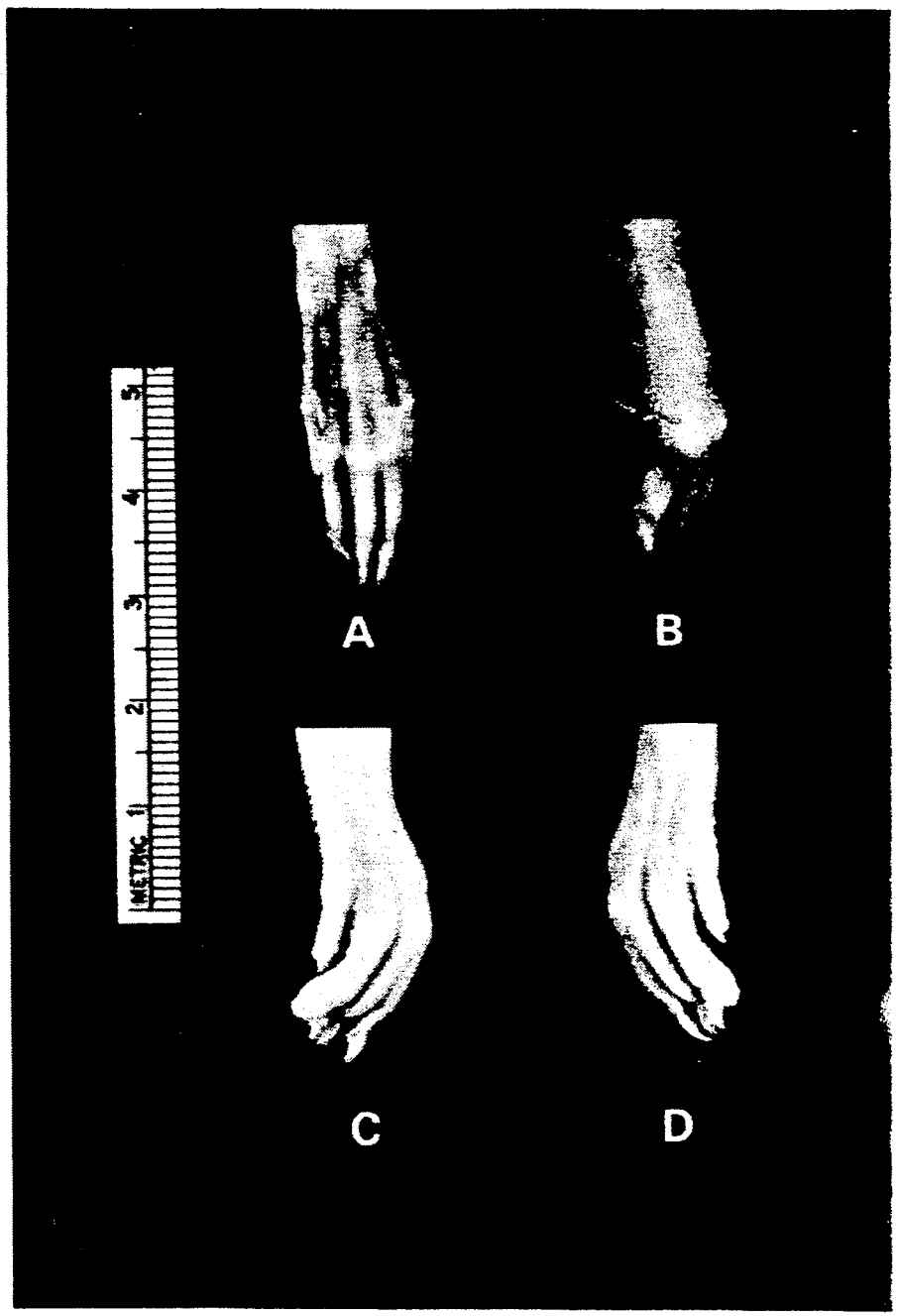
FIG. 1 shows the effect of antiflammin-1 on carragennin induced inflammation and edema in rat footpad; A=control without any injections; B=injected with 1% (0.1 cc) carrageenin solution (note the inflammation and edema); C=D=animal was injected with 0.2 cc of antiflammin-1 intravenously, then carrageenin was injected in the footpads (note the absence of edema and inflammation on both feet).

The above and various other objects and advantages of the present invention are achieved by providing synthetic polypeptides having amino acid sequence (single letter code) selected from the group consisting of MQMNKVLDS, HDMNKVLDL, MQMKKVLDS, DTMDAGMQMKKVLDS, GMASKAGAIAG, GIGKPLHSAG, GIGKPLHSAK, GWASKIGQTLG, GIGKFLHSAK, and GIGFLHSAG.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The term "anti-inflammatory amount" as used herein means the amount which reduces or alleviates inflammation in the tissue or body.

MATERIALS AND METHODS

Animals: Virgin New Zealand rabbits weighting 3-3.5 Kg were used for all experiments. These animals were housed in separate cages and provided with food and water ad libitum. A daily schedule of 12 hours light and 12 hours darkness was maintained throughout the experimental period.

Sprague Dawly rats of both sexes weighing about 175 to 200 grams were used for testing the anti-inflammatory effects of uteroglobin and antiflammins in carrageenan induced inflammation in the footpads of these animals. The animals were housed in groups of ten in each cage and provided with food and water ad libitum. A daily schedule of 12 hours of light and 12 hours of darkness was maintained throughout the experimental period.

Purification of uteroglobin: Uterglobin was purified according to the method of Nieto et al (*Arch. Biochem. Biophys.* 180:82-92, 1977) with minor modifications as described by Mukherjee et al, (*Am. J. Reprod. Immunol.* 2:135-141, 1982). Thus, uterine washings were obtained from rabbits primed with humam chorionic gonadotropin. The pooled uterine washings were then purified by Sephadex G-100 gel filtration which resulted in five distinct absorption peaks at 280 nm. Only the fifth peak contained significant amounts of uteroglobin as measured by a sensitive radioimmunoassay as described by Mayol et al, (*Endocrinology* 95:1534-1538, 1974). Upon further purification of the fifth peak on a CM-cellulose column, a homogeneous peak was obtained which was also positive for uteroglobin in the radioimmunoassay (RIA). This peak was further purified by Sephadex G-50 column chromatography. The resulting single peak obtained from this column contained substantially pure uteroglobin as evidenced by isoelectric focusing with a PI of 5.4, the known isoelectric point of uteroglobin. As a further check of purity, this protein was subjected to SDS-PAGE which yielded a single homogeneous band as previously reported (Mukherjee, et al, 1982, supra). The purified preparation of uteroglobin was lyophilized and used in all tests.

Synthesis of Antiflammins: Amino acid sequence of the antiflammins of the present invention allowed custom synthesis of these oligopeptides by commercially available, routine peptide synthesizer. Typically, the peptides were synthesized by solid-phase methods on a Biosearch Sam II synthesizer with manual addition of the amino acid derivatives. The synthesis was started with Boc O-Bzl Ser phenylacetamidomethyl resin (Omni Biochem) to which the Boc derivatives including beta-Bzl Asp (U.S. Biochemical Corp.) and 2-Cl-2 Lys (Bachem) were coupled as active esters formed by reaction with dicyclohexylcarbodiimide and hydroxybenzotriazole. The peptide was cleaved from the resin by treatment with hydrogen fluoride in the presence of anisole and ethyl methyl sulfide for 45 minutes at 4° C. The peptide was purified by semi-preparative chromatography. Sample loads of approximately 50 mg were chromatographed on a uBondapak $C_{18}$ 21×150 mm column (Waters/Millipore) at a flow of about 6 ml/min in 0.1% trifluoroacetic acid with a gradient of acetonitrile, 0% to 15% in 20 minutes, and continuing at 15% until total elution of material was obtained. The resulting peptide was homogeneous by analytical HPLC and amino acid analysis (Stewart et al, *Solid Phase Peptide Synthesis*, Pierce Chemical Co. Rockford Ill., 1984).

Induction of inflammation and the effect of uteroglobin: The dorsal skin of rabbits was shaved and ½ square inch areas demarcated lightly with a felt tip marker pen. The ink from this pen was tested prior to the initiation of these experiments and was found to be noninflammatory. The demarcated areas were used for identifying the locations where phorbol, carragennin, or other test substances were injected. Using a 25 gauge needle and a tuberculin syringe (1 cc), phorbol myristate acetate solution (10 mM) was injected into all areas, except for two, where no injections were given and two other areas where the solvent of phorbol myristate, dimethyl sulfoxide (DMSO), was injected alone. Various test substances were injected on one side of the vertebral column and the opposite side was used for controls. Thus, in this system a comparison of phorbol induced inflammation with the effects of various test substances could easily be made. These areas were observed daily and the diameter of the erythema and induration for each lesion was measured by the same observer. Some of the animals were sacrificed after 72 hours of injection and the demarcated areas of the skin were dissected out and fixed in 2.5% glutaraldehyde in cacodylate buffer (pH 7.4). These tissues were used for histopathological analysis.

A similar groups of animals were sacrificed 48 hours after the injections were made and the skin lesions were dissected out and homogenized in cold phosphate buffered saline (PBS, pH 7.4). The homogenate was centrifuged at 2500×g for 10 minutes at 4° C. The supernatants were frozen at −70° C. until assayed for prostaglandins. A radioimmunoassay (DeMars *Laboratory Medicine* pp. 1-23, 1974) was used for prostanoid determinations. A small aliquot (500 μl) was set aside from each sample and total proteins were determined by the method of Lowry et al, (*J. Biol. Chem.* 193:265-269, 1951).

Various peptides were dissolved in phosphate buffered saline at desired concentrations. A 1% carrageenan (0.1 cc) was used in all foot pad injection. Two sets of experiments were performed: (i) the animals were injected with carrageenan in both hind foot pads and 2 to 3 minutes later the desired peptide was injected to one foot while the other received an injection of equal amount of PBS and served as non-treated control; and (ii) peptide was injected intravenously through the dorsal tail vein 2-3 minutes prior to injection of carrageenan in one of the foot pads while the other received PBS as a control. The animals were sacrified 4 hours later and the foot dissected out at the angle of the ankle at the bony prominence. The weights were measured and recorded. This assay was standardized by using uninjected animals. The weights of the hind feet, when dissected as described, were found to be remarkably similar. After the weights were obtained, the feet were fixed in 2.5% glutaraldehyde in cacodylate buffer (pH 7.4) and were used for histopathological analysis.

Table 1 lists the amino acid sequences of various synthetic antiflammins and Table 4 shows relative $PLA_2$ inhibitory activity of representative antiflammins. It should be noted that the family of antiflammins of the present invention have potent $PLA_2$ inhibitory activity. It is further noted that when an ($NH_2$) group is added to the carboxy terminal, for example, to antiflammin 3, a total loss of $PLA_2$ inhibitory activity is observed at $10^{-3}M$ concentration as shown by the data in Table 4. Also various deletions from antiflammins 1 or additions to basic tetrapeptide (VLDS) resulted in total dissapearance of $PLA_2$ inhibitory activity (Table 4). These findings indicate that at least nine amino acids are required for antiflammin activity.

TABLE 1
AMINO ACID SEQUENCE OF ANTIFLAMMINS

| Peptide Designation | Amino Acid Sequence |
|---|---|
| Antiflammin-1 | MQMNKVLDS |
| Antiflammin-2 | HDMNKVLDL |
| Antiflammin-3 | MQMKKVLDS |
| Antiflammin-4 | DTMDAGMQMKKVLDS |
| Antiflammin-5 | GMASKAGAIAG |
| Antiflammin-6 | GIGKPLHSAG |
| Antiflammin-7 | GIGKPLHSAK |
| Antiflammin-8 | GWASKIGQTLG |
| Antiflammin-9 | GIGKFLHSAK |
| Antiflammin-10 | GIGKFLHSAG |

FIG. 1 demonstrates the effect of antiflammins (illustrated by antiflammin-1), on carragennin induced inflammation and edema in rat foot pads. The absence of edema and inflammation is noteworthy on both feet at 0.2 ml of 10 $\mu M$ solution of antiflammin-1 injected intravenously.

Figure 2:
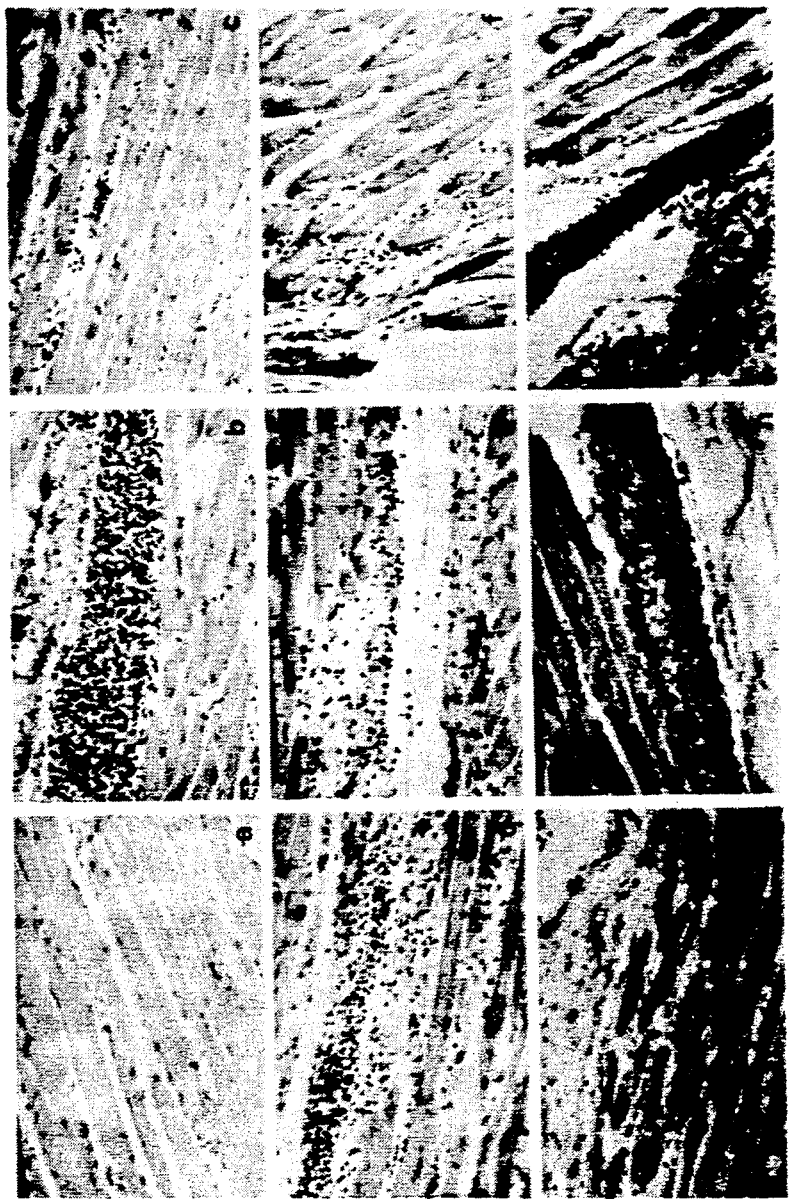
FIG. 2 are photomicrographs showing the effect of antiflammin-1 on carragennin induced inflammation in rat foot pads; a=control (no injection); b=carrageenin injected only; c=carrageenin injected, then treated with antiflammin 10 $\mu M$; d=carrageenin injected, then treated with Ibuprofen 10 $\mu M$; e=carrageenin injected, then treated with Dexamethasone 10 $\mu M$; f=carrageenin injected, then treated with antiflammin+Ibuprofen; g=carrageenin injected, then treated with Dexamethasone+antiflammin; h=carrageenin injected, then treated with a non-specific protein myoglobin; and i=carrageenin injected, then treated with antiflammin+arachidonate.

FIG. 2 presents histological evidence of the effect of antiflammin, with and without the combination of other agents, on carragennin induced inflammation in rat foot pads. The superior anti-inflammatory effect obtained with antiflammin alone at 10 $\mu M$ concentration compared to the same concentration of dexamethasone is remarkable. The results also indicate anti-inflammatory efficacy of a combination of antiflammin and dexamethasone.

Similar anti-inflammatory effects were observed when antiflammins were used in combination with ibuprofen. This combination was less effective as compared to the combination of dexamethasone and antiflammin, (FIG. 2). The anti-inflammatory effects of antiflammins were abolished when these substances were used in combination with equimolar amounts of arachidonate (FIG. 2) suggesting, again, that the antiflammins exert their effects predominantly by inhibiting phospholipase $A_2$ enzyme activity and not by inhibiting cyclo- or lipo-oxygenase enzymes as is the case in the action of nonsteroidal anti-inflammatory agents.

Figure 3:
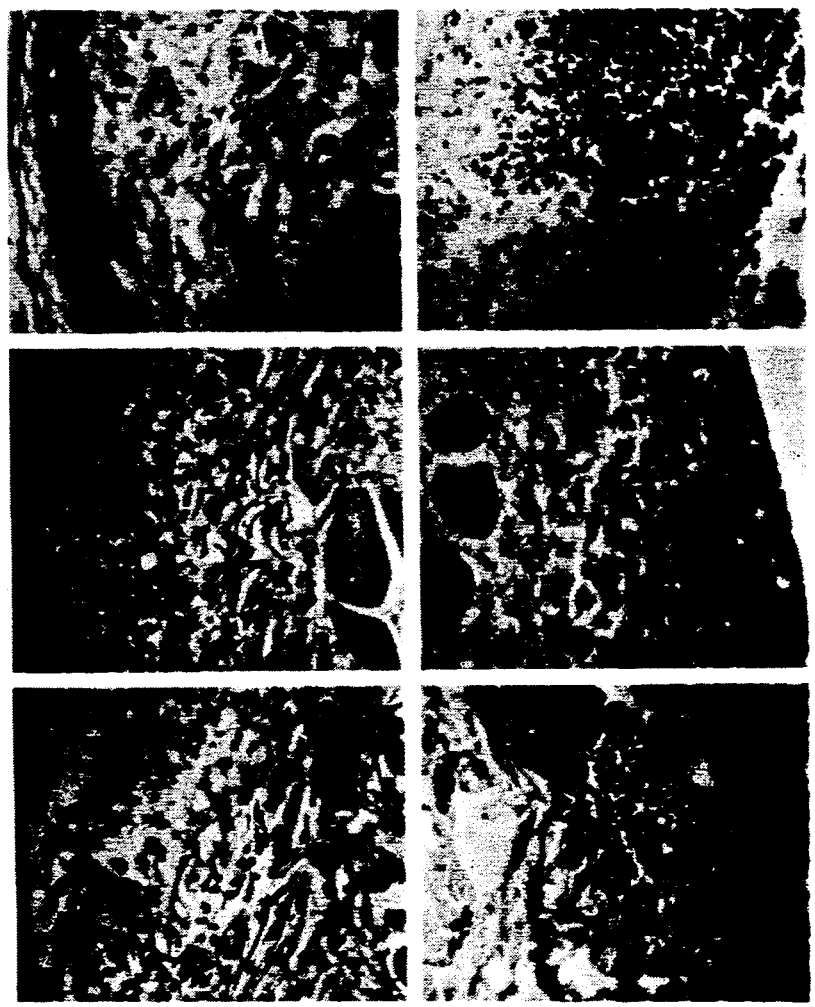
FIG. 3 are photomicrographs showing the effect of uteroglobin on phorbol myristate acetate induced inflammation on rabbit skin; A=control skin (no injection); B=phorbol injected (note the inflammatory response); C=uteroglobin (20 $\mu M$) injected after phorbol was injected (note the reduction of inflammatory cells in this site compared to B); D=Dexamethasone (20 $\mu M$) injected after phorbol was injected (note similar effect as in C); E=uteroglobin and Dexamethasone injected following phorbol injection (note the dramatic antiinflammatory response, only a few inflammatory cells could be seen in this site).

FIG. 3 and Table 2 show the effect of uteroglobin alone and in combination with other agents on phorbol induced inflammation. Table 3 shows the effect of uteroglobin alone and in combination with other agents on prostanoid levels in tissues injected with phorbol. The data clearly demonstrate the efficacy of uteroglobin as an anti-inflammatory agent. The data also show the additive effect of the combination of uteroglobin and dexamethasone.

Table 4 presents evidence that other similar appearing peptides have no $PLA_2$ inhibitory activity. It is important to note that the antiflammins of the present invention have one and a half times or more $PLA_2$ inhibitory activity compared to known polypeptides such as a PGL, magainins and the like (data not shown).

TABLE 2
Inhibition of photbol myristate acetate-induced inflammation by uteroglobin.

| Treatment | No Phorbol injected | | Phorbol injected | |
|---|---|---|---|---|
| | Erythema (mm) | Induration (mm) | Erythema (mm) | Induration (mm) |
| None | ND | ND | 29.3 ± 4 | 25.6 ± 2 |
| Phosphate Buffered Saline | ND | ND | 28.0 ± 3 | 26.0 ± 3 |
| Dimethylsulfoxide | 2 ± 0.5 | 1 ± 0.02 | 29.0 ± 4 | 26.0 ± 3 |
| Dexamethasone (20 $\mu M$) | ND | ND | 10.5 ± 1.2 | 8.1 ± 2.0 |
| Uteroglobin (20 $\mu M$) | ND | ND | 6.4 ± 0.5 | 5.1 ± 0.8 |
| Uteroglobin (20 $\mu M$) pre-treated with antibody | 1.5 ± 0.3 | ND | 23.7 ± 5.0 | 21.3 ± 3.4 |
| Uterglobin + Dexamethasone (1:1) | ND | ND | 2.5 ± 1.0 | 1.8 ± 0.6 |
| Uterglobin + Arachidonate (20 $\mu M$) | 1.9 ± 0.2 | 1.0 ± 0.5 | 21.4 ± 4.6 | 18.6 ± 1.8 |
| Dexamethasone + Arachidonate | 2.3 ± 0.4 | 2.0 ± 0.7 | 26.3 ± 7.3 | 22.4 ± 4.0 |

Phorbol myristate acetate concentration was 10 $\mu M$; the volume of injection was 0.1 ml for all substances.
ND = Nondetectable; the erythematous and indurated areas were outlined by a fine point felt pen and the diameter of the lesions were measured at 4 different points on the same lesion. The results are expressed as the mean of these determinations ± SEM.

TABLE 3
The effects of uteroglobin and dexamethasone on prostanoid levels in tissues injected with phorbol myristate acetate.

| Treatment+ | PROSTAGLANDIN LEVELS* (pg/mg protein) | |
|---|---|---|
| | $PGE_2$ | $PGF_2\alpha$ |
| 1. Control (No phorbol)§ | 60 | 45 |
| 2. Dimethylsulfoxide | 402 | 585 |
| 3. Phosphate buffered saline | 426 | 450 |
| 4. Uteroglobin (20 $\mu M$) | 94 | 58 |
| 5. Dexamethasone (20 $\mu M$) | 106 | 88 |
| 6. Uteroglobin + Dexamethasone | 65 | ND |
| 7. Uteroglobin + Arachidonate (20 $\mu M$) | 400 | 416 |
| 8. Dexamethasone + Arachidonate | 511 | 508 |
| 9. Dexamethasone + Uteroglobin + Arachidonate | 405 | 382 |

*The results are expressed as the mean of two experiments; ND = Nondetectable; + = Volume injected was 0.1 ml for each substance/site. Phorbol (10 $\mu M$) was injected first and after 5 minutes of this injection various test substances were injected at the same site. §= This is the only site where no phorbol was injected. All other areas were injected with phorbol first.

TABLE 4
PERCENT $PLA_2$ INHIBITORY ACTIVITY OF PREPRESENTATIVE ANTIFLAMMINS*

| Peptide Designation | Molarity | % $PLA_2$ Inhibition |
|---|---|---|
| Antiflammin-1 | $5 \times 10^{-8}$ | 89.6 |
| Antiflammin-2 | $5 \times 10^{-8}$ | 86.5 |
| Antiflammin-3 | $5 \times 10^{-8}$ | 81.6 |
| Antiflammin-4 | $10^{-3}$ | 48.0 |
| Antiflammin-5 | $5 \times 10^{-8}$ | 90.4 |

Figure 4:
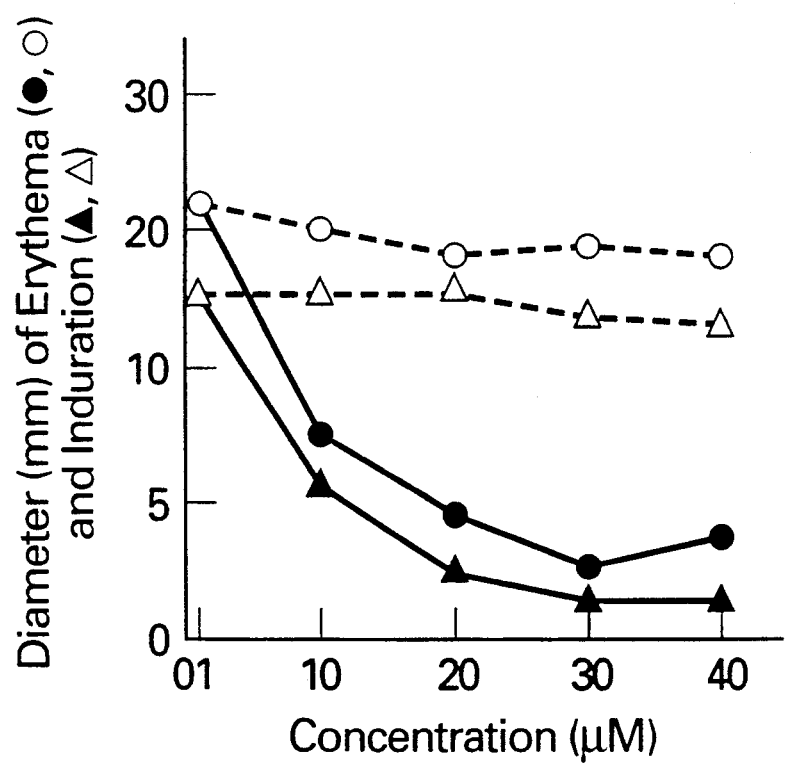
FIG. 4 shows the dose response curve of uteroglobin on phorbol myristate acetate induced erythema (●, ○) and induration (▲, △) in rabbit skin. Open circles and triangles indicate control treatment.

*Other peptides, for example KVLD, MKKVLD, MNKVLD, MQMKKVLDS($NH_2$) and GICPRFAHVI, when tested at $10^{-3}M$ concentration under the same conditions had no $PLA_2$ inhibitory activity Uteroglobin inhibits both erythema and induration induced by phorbol myristate acetate. FIG. 4 illustrates the dose response curve as related to erythema and induration. Significant inhibitory effect is produced at 10 $\mu M$ concentration of uteroglobin. However, the most dramatic effect is observed at a dose of 20 $\mu M$ of uteroglobin alone. Myoglobin was used as a nonspecific control and this protein did not have any suppressive effect on either erythema or induration induced by phorbol.

To determine the extent of the inflammatory reactions induced by phorbol and the inhibitory effect of uteroglobin histopathological assessment of the skin lesions was made. In FIG. 3, representative histological sections of the skin samples showing the effects of phorbol myristate acetate, uteroglobin, dexamethasone or dexamethasone plus uteroglobin are presented. Phorbol induced severe inflammatory reaction as evidenced by the accumulation of inflammatory cells. Although both uteroglobin and dexamethasone reduced the density of these inflammatory cells compared to the area of the skin treated with phorbol alone, the more pronounced results were obtained when uteroglobin was used in conjunction with dexamethasone similar to the effect produced with a combination of antiflammin with dexamethasone. Myoglobin injected as a nonspecific control did not have any inhibitory effect.

A quantitative determination of erythema and induration in these lesions were also performed. Measurements of the diameter of erythema and induration are presented in Table 2. Phorbol induced erythema within half an hour of injection and measurable induration appear within 12 hours. Uteroglobin as well as dexamethasone in equimolar concentrations dramatically reduced both erythema as well as induration. These effects were more pronounced when uteroglobin and dexamethasone were injected in combination. The inhibitory effect of both uteroglobin and dexamethasone was overcome by arachidonic acid injection into the lesions previously injected with either or both of these substances. Additionally, the inhibitory effects of uteroglobin were abolished when uteroglobin pretreated with its antibody was used (data not shown). Both arachidonic acid and DMSO induced some erythema and induration.

To determine whether the inflammatory reaction caused by phorbol was mediated by prostaglandins (PG) and whether uteroglobin affected these levels, the tissue level of prostanoids were determined. Both $PGE_2$ and $PGF_{2\alpha}$ levels were determined in the skin lesions. These results are presented in Table 3. The control skin without phorbol injection had a very low level of the prostaglandins. Phorbol injection increased $PGF_{2\alpha}$ approximately 10-fold and $PGE_2$ 8-fold compared to the control values. Uteroglobin dramatically reduced these prostanoid levels as did dexamethasone. Again, uteroglobin and dexamethasone together had an additive effect on prostanoid levels. Injection of arachidonate with either dexamethasone or uteroglobin abolished the inhibitory effects of these substances.

It is clear from these results that both, uteroglobin and antiflammins are potent anti-inflammatory agents and antiflammins, in nM amounts, are also potent $PLA_2$ inhibitor.

Of course, a pharmaceutical composition comprising as an active ingredient anti-inflammatory amount of antiflammin, alone or in combination with other anti-inflammatory agent, such as dexamethasone, in a pharmaceutically acceptable, non-toxic, sterile carrier can be easily prepared in accordance with the present invention. The combination can be for local or systemic use and may be in any suitable form such as an injectable liquid, ointment, paste, tablet and the like which are prepared following standard techniques with or without filler materials or vehicles well known to one of ordinary skill in the art.

The invention also provides a method of treating inflammation, comprising administering to a host or contacting a tissue afflicted with inflammation, an anti-inflammatory effective amount of antiflammin or uteroglobin to reduce inflammation. The antiflammins or uteroglobin could, of course, also be combined with other compatible additives and the like well known to one of ordinary skill in the art.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A antiflammin peptide selected from the group consisting of MQMNKVLDS, HDMNKVLDL, MQMKKVLDS and DTMDAGMQMKKVLDS.

2. The antiflammin peptide of claim 1 which is MQMNKVLDS.

3. The antiflammin peptide of claim 1 which is HDMNKVLDL.

4. The antiflammin peptide of claim 1 which is MQMKKVLDS.

5. The antiflammin peptide of claim 1 which is DTMDAGMQMKKVLDS.

6. A pharmaceutical composition for treating inflammation comprising a peptide of claim 1 and a pharmaceutically acceptable carrier.

7. The pharmaceutical composition of claim 6 further comprising an anti-inflammatory effective amount of dexamethasone or ibuprofen.

8. A method of treating inflammation in a patient comprising administering to the patient an anti-inflammatory effective amount of a peptide chosen from the group consisting of MQMNKVLDS, HDMNKVLDL, MQMKKVLDS, DTMDAGMQMKKVLDLS, GMASKAGAIAG, GIGKFLHSAK and GIGKFLHSAG.

9. A method of treating inflammation in a patient comprising administering to the patient an anti-inflammatory effective amount of a peptide of claim 8 mixed with an anti-inflammatory effective amount of dexamethasone or ibuprofen.

* * * * *